(12) United States Patent
Rapoport

(10) Patent No.: US 7,880,467 B2
(45) Date of Patent: Feb. 1, 2011

(54) PACKED ARRAY OF MRI/NMR DEVICES AND AN MRI/NMR METHOD OF ANALYZING ADJACENT LINES OF GOODS SIMULTANEOUSLY

(75) Inventor: Uri Rapoport, Moshave Ben Shemen (IL)

(73) Assignee: Aspect Magnet Technologies Ltd., Moshav Ben Shemen (IL)

( * ) Notice: Subject to any disclaimer, the term of this patent is extended or adjusted under 35 U.S.C. 154(b) by 0 days.

(21) Appl. No.: 11/184,249

(22) Filed: Jul. 19, 2005

(65) Prior Publication Data

US 2006/0279281 A1    Dec. 14, 2006

Related U.S. Application Data

(60) Provisional application No. 60/688,761, filed on Jun. 9, 2005.

(51) Int. Cl.
*G01V 3/00* (2006.01)
(52) U.S. Cl. .................................. 324/309; 324/307
(58) Field of Classification Search .......... 324/300–322
See application file for complete search history.

(56) References Cited

U.S. PATENT DOCUMENTS

| | | | |
|---|---|---|---|
| 4,514,691 A * | 4/1985 | De Los Santos et al. .... | 324/301 |
| 5,490,513 A * | 2/1996 | Damadian et al. ........... | 600/415 |
| 6,302,579 B1 * | 10/2001 | Meyer et al. ................. | 378/196 |
| 6,522,145 B1 * | 2/2003 | Damadian et al. ........... | 324/318 |
| 6,549,799 B2 * | 4/2003 | Bock et al. .................. | 600/422 |
| 6,643,799 B1 * | 11/2003 | Bonissone et al. ........... | 714/26 |
| 6,668,403 B2 * | 12/2003 | Seufert ......................... | 5/601 |
| 6,972,565 B2 * | 12/2005 | Yokoi et al. ................. | 324/307 |
| 7,084,627 B2 * | 8/2006 | McKendry et al. .......... | 324/308 |
| 7,127,499 B1 * | 10/2006 | Accardi et al. .............. | 709/219 |
| 7,345,478 B2 * | 3/2008 | Lieblich et al. ............. | 324/300 |
| 7,355,402 B1 * | 4/2008 | Taicher et al. ............... | 324/300 |
| 7,400,147 B2 * | 7/2008 | Rapoport .................... | 324/318 |
| 2002/0030491 A1 * | 3/2002 | Kose .......................... | 324/318 |

FOREIGN PATENT DOCUMENTS

| | | | |
|---|---|---|---|
| JP | 07198636 | * | 7/1995 |
| JP | 09297113 | * | 9/1997 |
| JP | 9297113 | | 11/1997 |
| JP | 11142354 | | 5/1999 |
| JP | 11142354 | * | 11/1999 |
| JP | 7198636 | | 1/2005 |

* cited by examiner

*Primary Examiner*—Melissa J Koval
*Assistant Examiner*—Dixomara Vargas
(74) *Attorney, Agent, or Firm*—Gottlieb, Rackman & Reisman, P.C.

(57) ABSTRACT

An industrial quality and process control (QPC) system, includes inter alia at least one packed array of MRI/NMR devices of substantially no fringing magnetic fields, adapted to analyze adjacent lines of goods simultaneously.

21 Claims, 2 Drawing Sheets

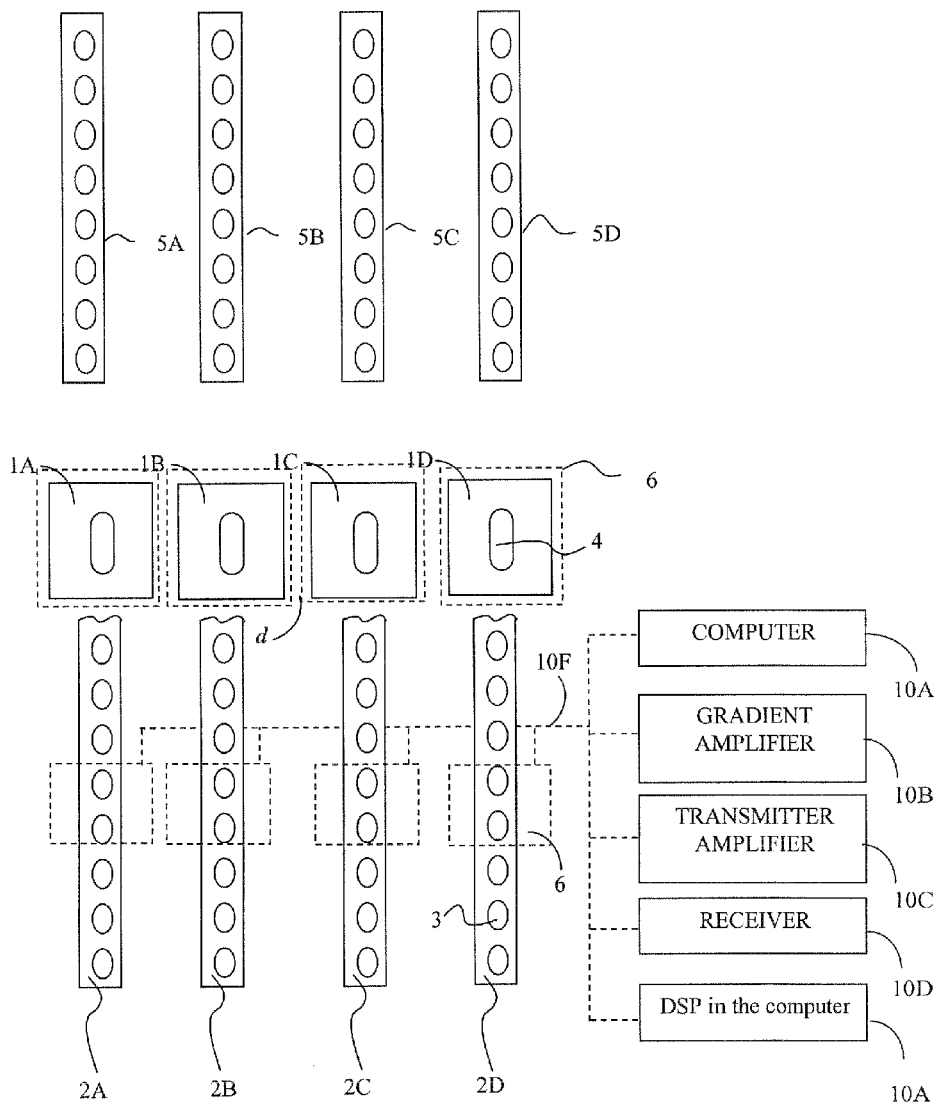
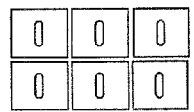
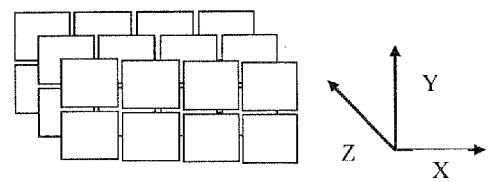
Fig. 1
Fig. 2A　　Fig. 2B　　Fig. 2C

PACKED ARRAY OF MRI/NMR DEVICES AND AN MRI/NMR METHOD OF ANALYZING ADJACENT LINES OF GOODS SIMULTANEOUSLY

CROSS REFERENCE TO RELATED APPLICATION

The present application claims priority to U.S. Provisional Application No. 60/688,761 dated Jun. 9, 2005.

FIELD OF INVENTION

The present invention generally relates to a packed array of MRI/NMR devices and a MRI/NMR method of providing industrial quality and process control for a plurality of adjacent lines of goods simultaneously.

BACKGROUND OF THE INVENTION

Most of the commercially available MRI and NMR devices generate a powerful external magnetic field while analyzing items in their inner volume. Such undesired fringing magnetic fields eliminate the option of installing MRI/NMR device side-by-side. Now days, significantly reduced magnetic forces are obtained outside few MRI/NMR device, i.e., ASPeCT™ devices, suggested to achieve up to two Tesla magnetic field with uniformity suitable for sub-ppm NMR and MRI analysis and over 400 mm usable air gap between the pole pieces. The purpose of the present invention is to provide a novel industrial analysis means and method applicable by the same.

SUMMARY OF THE INVENTION

It is therefore one object of the present invention to present an industrial quality and process control (QPC) and process control system, comprising inter alia at least one packed array of MRI/NMR devices of substantially no fringing magnetic fields, adapted to analyze lines of goods simultaneously. This system is comprised of a plurality of magnets installed side by side with virtually zero gap between the magnets, and thus it is utilizable in an industrial environment whereat goods selected in a non-limiting manner from products, materials, bulk of powders, a predetermined measure of liquids etc in the upstream or downstream production stages are placed on a conveyor belt or the like, or in pipes or the like, and maneuvered simultaneously towards the magnets for analysis.

Another object of the present invention is to disclose a cost effective and industrially oriented method of analyzing a multiple lines of goods simultaneously. This method and system are adapted to save installation space, provided with a large system output, i.e., effectively analyze lines of good in parallel.

BRIEF DESCRIPTION OF THE FIGURES

In order to understand the invention and to see how it may be implemented in practice, preferred embodiments will now be described by way of non-limiting example only, with reference to the accompanying drawing, in which:

FIG. 1 presents a packed array of MRI/NMR devices according to one embodiment of the present invention, adapted for analyzing adjacent lines of goods simultaneously;

FIGS. 2A-2C schematically illustrates various stacks of MRI/NMR devices according to another embodiment of the present invention, wherein in FIG. 2A i=2, x=2, y=1 and z=0; in FIG. 2B i=6, x=3, y=2 and z=0; and in FIG. 2C i=24, x=4, y=3 and z=2;

DETAILED DESCRIPTION OF THE EMBODIMENTS

Figure 3:
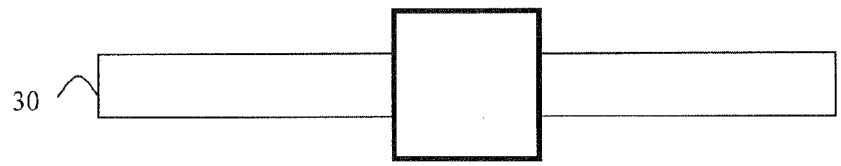
FIG. 3 includes a side plan view showing a pipe and a side plan view showing a conduit of embodiments of the present invention.
Figure 3:
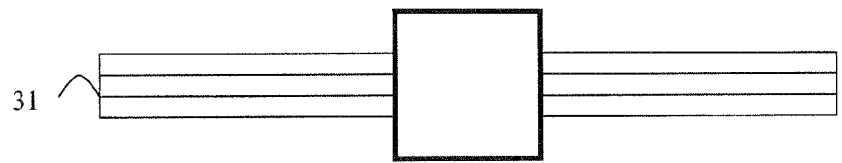
Figure 4:
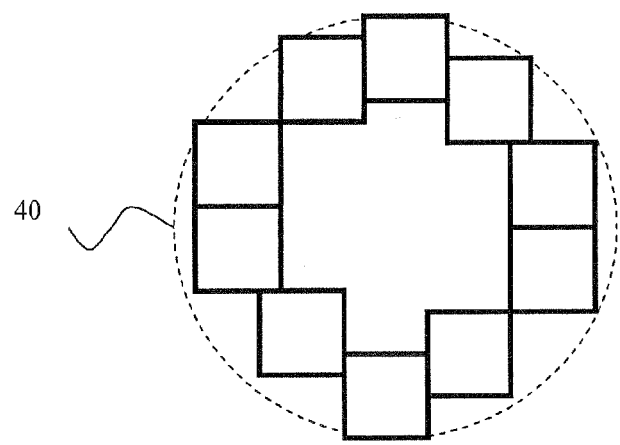
FIG. 4 is a side view showing a circularly shaped array of one embodiment of the present invention.

The following description is provided, alongside all chapters of the present invention, so as to enable any person skilled in the art to make use of said invention and sets forth the best modes contemplated by the inventor of carrying out this invention. Various modifications, however, will remain apparent to those skilled in the art, since the generic principles of the present invention have been defined specifically to provide a novel industrial QPC system. This system comprising inter alia at least one packed array of i MRI/NMR devices of substantially no fringing magnetic fields, adapted to analyze up to i lines of goods simultaneously, wherein i is an integer number higher or equal 2.

It is in the scope of the present invention wherein said packed array is a stack comprising a plurality of i MRI/NMR devices, characterized by the dimensions of x, y and z MRI/NMR device; and further wherein i is an integer number higher or equal 2, and x, y and z are integer numbers higher or equal 0, such that in case those values higher or equal 1, $x*y*z$ equals i. The shape of at least a portion of the stack is preferably polygonal, circular or any combination thereof.

The term 'packed array' refers hereinafter to an array of two or more MRI/NMR devices of substantially no fringing magnetic fields, wherein the distance between said devices is respectively small, such that a plurality of feeding lines are directed to said array, and a rapid analysis of a mass (i.e., industrial scale) of goods is provided simultaneously.

The term 'industrial QPC system' refers hereinafter to at least one packed array of MRI/NMR devices adapted to analyze the properties, compositions or shape of goods, as well as processes and reactions wherein the terms 'analysis' and/or 'QPC' are denoted hereinafter to any detection, analysis, control, measurement, study, observation or study of a given matter or process by a means of a MRI/NMR device.

It is also in the scope of the present invention wherein at least a portion of the goods are fed into the MRI/NMR devices by means of a conveyor belt or the like, by means of tunnels, conduits or pipes or any combination thereof. The system is further adapted to operate either continuously or in a batch wise manner.

It is also in the scope of the present invention wherein the magnets of the MRI/NMR devices are passively shielded and/or actively shielded by means of an RF and/or magnetic shielding.

The QPC system defined above is preferably comprising additional computerized means, adapted for time sharing of at least one of the group consisting in a non-limiting manner gradient power supplying; RF transmitting and/or amplifying; RF receiving; digital signal processing or any combination thereof.

Reference is made now to FIG. 1, schematically presenting an industrial QPC system, comprising inter alia at least one array of MRI/NMR devices of substantially no fringing magnetic fields (1A-1D). Here the MRI/NMR devices are arranged in parallel such that the distance (d) between devices (1A-1D) is short and determined mainly by the feeding requirements, e.g., the optimum distance between the various feeding conveyor belts (e.g., 2B and 2C).

According to this example and in a non-limiting manner, said four MRI/NMR devices (1D-1D) are fed by four parallel conveyor belts (2A-2D), each conveyor transports into one of the MRI/NMR devices a continuous, segmented or pulsed series of goods (3) to be examined.

Various models are possible, such as a sorting facility adapted for sorting incubator's avian eggs, e.g., divide lines of eggs to gender of the embryo; a system adapted for selective elimination of fertilized eggs from product line, evacuating eggs characterized with improper size or condition, or provided with predetermined physiological condition.

Another example is sorting fruits and other agricultural products and raw materials, and especially utilizing in citrus packing house to be QPC for the inspection of presence of seeds, presence of a hollow core inside the fruit, defining over ripped stages, mold damages, freeze damages sugar level, water level and pH etc. This example is further provided useful for other feeding systems, such as wherein the goods are in a liquid state, e.g., QPC of oil refinery industry; wherein multiple pipes comprising flowing oil in its various refining process is enforce to flow into the MRI/NMR devices for analysis. According to this embodiment of the present invention, each feeding line (e.g., 2D) is entering the MRI/NMR device (1D, frontal view) via at least one inflow aperture (4), and exiting (5D) said MRI/NMR device via at least one outflow aperture (not shown). The QPC is provided either continuously or in a batch wise manner, e.g., by stopping the line to a predetermined short period of times before MRI/NMR analysis the goods.

It is hence according to one aspect of the present invention wherein the QPC as defined above is adapted for sorting incubator's avian eggs, and especially sorting the gender of embryo; selectively eliminating fertilized eggs from product line; or evacuating eggs characterized with improper size or physiological condition or any combination thereof.

It is hence according to another aspect of the present invention wherein the QPC as defined above is adapted for sorting fruits and other agricultural products and raw materials, and especially for utilizing in citrus packing house to inspect presence of seeds, locating a hollow core inside the fruit, defining over ripped stages, scanning mold damages, determining freeze damages sugar level, evaluating water level or determining fruit's acidity or any combination thereof.

It is according to yet another embodiment of the present invention wherein the said MRI/NMR enabled QPC is further comprising computerized means (10A), enabling inter alia time sharing of gradient power supply (10B), time sharing of RF transmitter and/or amplifier (10C), time sharing of RF receiver (10D), time sharing of digital signal processing (10). Said QPC is preferably yet not exclusively provided by window (6, top view). It is acknowledged in this respect that any combination of time sharing as defined above with one, few or all MRI/NMR devices is possible.

Reference is made now to FIGS. 2A, 2B and 2C illustrating in a non-limiting manner various stacks, wherein 2A and 2B describes a front view of a polygonal stack, and FIG. 2C presents a lateral view of the same.

It is further in the scope of the present invention wherein the analyzed goods are either solid or liquid matter; and especially wherein the analyzed goods are selected from agricultural raw materials or products, cosmetics, chemicals, powders, gases, enveloped items, medicaments, industrial matters, metal ware or any other continuous or discrete members or combination of solid, liquid and gas.

The present invention also discloses a cost effective method of analyzing a multiple lines of goods simultaneously. This method comprising inter alia the steps of obtaining at least one packed array of MRI/NMR devices of substantially no fringing magnetic fields; feeding said goods into said MRI/NMR devices, each line is directed towards a single device; analyzing said goods by said MRI/NMR devices; and then evacuating said goods from the MRI/NMR devices.

This method is especially useful wherein it comprises the step or steps of feeding the goods into the MRI/NMR devices by means of a plurality of conveyor belts or the like, or by a means of plurality of tunnels, conduits or pipes. Hence, the feeding of analyzed goods is adapted for either solid and/or liquid matter or gas It is in the scope of the present invention wherein the feeding and/or analyzing steps are provided either continuously or batch wise. This method may additionally comprise passive and/or active shielding of the MRI/NMR's magnets by RF and/or magnetic shielding means. Moreover, the method may additionally comprise of the step or steps of time sharing of at least one of the group of gradient power supplement; RF transmitter and/or amplifier; RF receiver; digital signal processing means or any combination thereof.

The invention claimed is:

1. An industrial quality and process control (QPC) system adapted to analyze adjacent lines of goods, said QPC comprising at least one packed array of MRI/NMR devices, said packed array comprising a plurality of i adjacently positioned MRI/NMR devices installed side by side with virtually zero gap between the magnets; said array characterized by dimensions of x, y, and z, where i is an integer not less than 2, and x, y, and z are integers not less than 0; wherein each of said MRI/NMR devices provides magnetic shielding from the other MRI/NMR devices and wherein each MRI/NMR device comprises a magnet, a gradient coil, and an RF coil such that said QPC system comprises in total not less than i independent magnets, i independent gradient coils, and i independent RF coils; further wherein the analysis of said lines of goods is performed simultaneously and independently by each of said MRI/NMR devices.

2. The QPC system according to claim 1, wherein the shape of the stack is polygonal, circular or any combination thereof.

3. The QPC system according to claim 1, wherein at least a portion of the goods are fed into the MRI/NMR devices by means of a conveyor belt.

4. The QPC system according to claim 1, wherein at least a portion of the goods are fed into the MRI/NMR devices by means of tunnels, conduits, or pipes.

5. The QPC system according to claim 1, wherein said QPC system is operated either continuously or batchwise.

6. The QPC system according to claim 1, wherein the magnets of the MRI/NMR devices are passively shielded by RF and/or magnetic shielding.

7. The QPC system according to claim 1, wherein the magnets of the MRI/NMR devices are actively shielded by RF and/or magnetic shielding.

8. The QPC system according to claim 1, additionally comprising computerized means adapted for time sharing of at least one of the group of means consisting of gradient power supplying means; RF transmitting and/or amplifying means; RF receiving means; digital signal processing means; and any combination thereof.

9. The QPC system according to claim 1, wherein the analyzed goods are chosen from the group consisting of solid matter and liquid matter.

10. The QPC system according to claim 1, wherein the analyzed goods are chosen from the group consisting of agricultural raw materials, agricultural products, cosmetics, chemicals, powders, enveloped items, medicaments, industrial goods, metalware, and any other continuous or discrete members.

11. A method of analyzing multiple adjacent lines of goods simultaneously, comprising steps of:
   a. obtaining at least one QPC according to claim 1;
   b. feeding said goods into said MRI/NMR devices, each line being directed towards a single device;
   c. analyzing said goods by use of said MRI/NMR devices; and,
   d. evacuating said goods from said MRI/NMR devices.

12. The method according to claim 11, further comprising an additional step of feeding said goods into said MRI/NMR devices by means of a plurality of conveyor belts.

13. The method according to claim 11, further comprising an additional step of feeding said goods into said MRI/NMR devices by means of a plurality of tunnels, conduits, or pipes.

14. The method according to claim 11, wherein at least one of said steps of feeding and analyzing is performed in a manner chosen from the group consisting of continuously and batchwise.

15. The method according to claim 11, additionally comprising a step of passively shielding the magnets of said MRI/NMR devices by RF and/or magnetic shielding means.

16. The method according to claim 11, additionally comprising a step of actively shielding the magnets of said MRI/NMR devices by RF and/or magnetic shielding means.

17. The method according to claim 11, additionally comprising a step of time sharing of at least one of the group of means consisting of gradient power supplying means; RF transmitting and/or amplifying means; RF receiving means; digital signal processing means; and any combination thereof.

18. The QPC system according to claim 1, additionally comprising feeding means adapted for feeding goods in a form chosen from the group consisting of solid, liquid, gaseous, and any combination thereof.

19. The QPC system according to claim 1, adapted for sorting avian eggs, wherein said sorting comprises sorting said eggs according to at least one criterion chosen from the group consisting of (a) the gender of the embryo within said eggs; (b) fertility of said eggs; and (c) size of said eggs and especially sorting the gender of embryo; selectively eliminating fertilized eggs from product line; or evacuating eggs characterized with improper size or physiological condition or any combination thereof.

20. The QPC system according to claim 1, wherein said goods are chosen from the group consisting of fruits, non-fruit agricultural products, and agricultural raw materials, and further wherein said analysis is chosen from the group consisting of (a) determining the presence of seeds; (b) locating a hollow core within a piece of fruit; (c) determining whether or not said goods are overripe; (d) analyzing for mold damage; (e) analyzing for damage due to freezing; (f) determining the sugar level; (g) determining the water level; (h) determining the acidity; and (i) any combination thereof.

21. An industrial quality and process control (QPC) system adapted to analyze adjacent lines of goods, said QPC comprising a plurality of i MRI/NMR devices installed side by side with virtually zero gap between the magnets; wherein each of said MRI/NMR devices provides magnetic shielding from the other MRI/NMR devices; and wherein each MRI/NMR device includes a magnet, a gradient coil and an RF coil such that said QPC system includes no less than i independent magnets, i independent gradient coils, and i independent RP coils; and further wherein each MRI/NMR device receives goods from at least one of said adjacent lines of goods and is adapted to analyze said goods and outputs of said goods wherein said analysis is performed independently of the other MRI/NMR devices.

* * * * *